US006998481B2

(12) United States Patent
Erdmann et al.

(10) Patent No.: US 6,998,481 B2
(45) Date of Patent: Feb. 14, 2006

(54) PROCESS FOR THE PREPARATION OF β-MANNITOL FOR DIRECT COMPRESSION

(75) Inventors: Martin Erdmann, Gross-Gerau (DE); Walter Hamm, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 522 days.

(21) Appl. No.: 10/317,196

(22) Filed: Dec. 12, 2002

(65) Prior Publication Data

US 2003/0114717 A1    Jun. 19, 2003

(30) Foreign Application Priority Data

Dec. 13, 2001    (DE) ................................ 101 61 402

(51) Int. Cl.
  *C07C 31/26* (2006.01)
  *B01J 2/00* (2006.01)
(52) U.S. Cl. .................... 536/124; 536/123.1; 424/464; 424/489; 264/109
(58) Field of Classification Search ................ 536/124, 536/123.1; 424/464, 489; 264/109
See application file for complete search history.

(56) References Cited

*Primary Examiner*—James O. Wilson
*Assistant Examiner*—Ganapathy Krishnan
(74) *Attorney, Agent, or Firm*—Millen, White, Zelano, Branigan, P.C.

(57) ABSTRACT

The present invention relates to a process for the preparation of mannitol for direct compression having a content of the β-modification of greater than 90%.

23 Claims, 2 Drawing Sheets

PROCESS FOR THE PREPARATION OF β-MANNITOL FOR DIRECT COMPRESSION

Figure 1:

The present invention relates to a process for the preparation of mannitol for direct compression having a content of the β-modification of greater than 90%.

In the production of tablets, D-mannitol can be employed as excipient material for an active ingredient. To this end, the D-mannitol is usually converted into a pulverulent form by a plurality of process steps with corresponding interim checks in order to enable it to be handled for tablet pressing and at the same time to facilitate binding-in of active ingredient.

U.S. Pat. No. 3,145,146 A discloses a spray-drying process by means of which mannitol is obtained in the form of fine particles having an average diameter of from 5 to 150 μm. A mannitol solution is spray-dried by atomisation into a stream of hot gas. The particles obtained are separated off by suitable measures.

It has also been disclosed that pulverulent D-mannitol can be prepared by granulation in a fluidised bed, in which the stream of process air flows through a specially shaped impingement plate, producing a fluidised bed from solid starting material. The spray liquid passes into the fluidisation space in finely divided form through a nozzle system. The fluidising particles are wetted, the surface is partially dissolved, and the particles adhere to one another. Solid is withdrawn continuously at the end of the fluidised bed. At the same time, a relatively small amount of solid, onto which spray liquid is finely distributed, is fed in at the inlet. A filter system prevents dust from leaving the fluidised bed, and only granule particles which have a minimum size are withdrawn at the outlet. In addition, solid particles which have a more or less random shape form in a fluidised bed of this type. Corresponding plants are marketed by various manufacturers.

The preparation of pulverulent mannitol is usually followed by a process step by means of which a powder having a uniform particle size distribution is obtained. This process step can include both grinding and screening (classification) of the powder. In the case of the use of mannitol as excipient material for pharmaceutical active ingredients, any additional process step in the preparation represents to the person skilled in the art a possible risk of the introduction of undesired impurities into the product.

It is furthermore known from the literature that D-mannitol can exist in polymorphic crystal forms; these can be the α-, β- and δ-forms. The definitions and characterisations used here correspond to the classification of polymorphic forms by X-ray structural analysis (X-ray diffraction pattern) given in Walter Levy, L.; Acad. Sc. Paris, t. 267 Series C, 1779 (1968). The β-form is the most stable form, although conversions into the other forms are possible depending on the storage time and the ambient conditions. For commercial applications, it is therefore desirable to obtain mannitol in the β-form, owing to its stability, directly in the preparation, since the product properties change to the least possible extent due to storage in this case.

It is furthermore known that on the one hand the polymorphic form in which the pulverulent D-mannitol exists and on the other hand the manner in which the particle structure of the individual particles has been built up are of importance for the compression properties of the pulverulent D-mannitol.

WO 97/38960 A1 describes that improved compression properties arise through partial or complete conversion of the pulverulent D-mannitol from the δ-form into the β-form. Conversion from the δ-form into the β-form is caused by targeted wetting of the particle surfaces of the powder with a water-soluble solvent or water and by subsequent drying. The percentage of β-mannitol formed is dependent on the amount of solvent employed and the duration of the drying operation. A mixture of δ- and β-forms is therefore usually present in the product.

It is disadvantageous in this process that the conversion is an additional process step which follows the actual powder preparation, and the drying requires at least 8 hours, during which the plant has to be continuously supplied with thermal energy.

The object of the present invention is therefore to provide a process which can be carried out in a simple manner and by means of which a mannitol for direct compression can be prepared in the β-modification in a single working step.

The object is achieved by a process for the preparation of mannitol for direct compression having a content of the β-modification of greater than 90%, characterised in that a) in a first step, an aqueous D-mannitol solution as starting material, spray gas, pulverulent β-mannitol and hot gas are combined, b) the resultant pulverulent product is precipitated into a fluidised bed, taken up, fluidised, and transported further.

Some of the pulverulent product formed can be recycled into the process.

In a particular embodiment of the process, the resultant powder is, in one or more granulation step(s), sprayed with further liquid medium, dried and transported further in the fluidised bed.

For the preparation of the mannitol solution, use is made of D-mannitol having a purity of >90%, preferably >95%. Use is preferably made of D-mannitol having a purity of >98%.

Surprisingly, the equilibrium can be shifted towards the formation of β-mannitol by recycling the β-mannitol formed as the dust fraction from the product discharge zone of the processor into step a) of the spray drying. In a particularly advantageous embodiment of the process, β-mannitol having a mean particle size of less than 20 μm, in particular having a mean particle size in the range from about 1 to 20 μm, preferably in the range from 3 to 15 μm, is recycled.

The recycling of the "dust-form" β-mannitol formed as pulverulent β-mannitol from the powder metering device in line (9A) is effected by controlling the rotational speed of the star valve 10A via the fan (E) into the spray drying (step a).

After the equilibrium has been established, it is readily possible to recycle pulverulent β-mannitol having a mean particle size of less than 75 μm, but in particular also pulverulent unground β-mannitol.

The particular design of the plant used enables the recycled pulverulent material to be comminuted, before the recycling, by grinding in the fan (E), which simultaneously serves as conveying element for the powder recycling.

Regulation of the rotational speeds of the star valves 10A and 10B of the plant used and grinding of the coarse (oversize) product formed to particle sizes of less than 75 μm in the fan (E) before recycling into the spray drying result in the exclusive formation of β-mannitol.

In order to carry out the process, an aqueous 40–50% D-mannitol solution is employed as starting material and is atomised at a temperature in the range from 60 to 100° C.

Air or an inert gas selected from the group consisting of $N_2$ and $CO_2$ can be used both as spray gas and as carrier and heating gas. The gas is preferably circulated in the process according to the invention, and the circulated gas is freed from particles by filters, dried in the condenser and fed back to the spray nozzles or heated and introduced into the fluidised bed.

The circulated gas is preferably freed from particles with the aid of dynamic filters.

In a particular embodiment of the process, the liquid media used have different compositions at different points of the plant.

Particle sizes of between 50 and 1000 μm can be produced specifically in the process according to the invention by varying the process parameters of spray pressure, spray amount, mannitol concentration, amount of powder recycled, hot-air stream and hot-air temperature.

For this purpose, the air fed to the plant is, in accordance with the invention, pre-heated to a temperature in the range 45–110° C. and the amount of feed air supplied is set in the range 1000–2000 $m^3/m^2$ per hour, giving a waste-air temperature in the range 30–50° C. At the same time, the spray pressure of the two-component nozzles is set in the range 2–4 bar, so that from about 1.5 to 3 $m^3$/(h kg of solution) of hot gas are fed to the two-component nozzle, with the temperature of the hot gas being set in the range from about 70 to 110° C. Good process results are obtained if the powder recycling is regulated in such a way that recycling is carried out in an amount in the range 0.5–2.0 kg of solid/(h kg of solution).

Particularly uniform formation of pulverulent product having a β-mannitol content of >95% is carried out by adjustment of the parameters of spray pressure, amount of liquid, mannitol concentration, amount of powder recycled, hot-air stream and hot-air temperature, through which the amount of powder present in the fluidised bed is set to an amount in the range 50–150 $kg/m^2$ of bed.

Experiments have found a process for the preparation of pure β-(D)-mannitol by means of which mannitol for direct compression (DC mannitol) having a suitable homogeneous particle size distribution can be prepared. The process is carried out using mannitol having a purity of greater than 98%, where the remainder can be sorbitol and other residual sugars. An aqueous solution having a mannitol content of about 40–50% by weight is prepared. This solution is atomised in a spray-drying plant at a feed-air temperature of about 60–95° C. and dried.

The process is carried out using a plant as described in DE 1 99 27 537, but with a slight modification. By means of the plant described in this patent application, it is possible per se to vary the properties of spray-dried or granulated, pulverulent products as desired with respect to particle size, particle size distribution, moisture content and compressibility. However, the changes to the plant enable additional fine adjustment through the powder recycling.

In particular, the process is carried out in a spray-drying plant which comprises a) a spray-drying unit (B), b) a fluidised bed (A), c) one or more additional spray or atomisation nozzles for liquid media (C), e) a powder-metering device (D) and f) a powder recycling system (9) with fan (E), where the lines (9A) and (9B) intended for powder recycling are provided with star valves (10A, 10B), and the powder (8) which does not enter the powder-metering device can be separated into a dust-form fraction and a coarse fraction.

In the spray-drying unit (B) of the plant used in accordance with the invention, the liquid medium (5), spray gas (6), pulverulent material (9) and hot gas (4) are combined.

In a particular embodiment, a spray-drying unit (B) is located vertically above a subsequent fluidised bed in a spray tower.

In a particular embodiment, the spray-drying unit (B) of the plant can comprise a spray system which consists of a two-component spray nozzle heated by means of hot water with coaxially arranged powder recycling and surrounding hot-gas flow.

In the plant used, one or more additional spray or atomisation nozzles for liquid media (C) can be installed in the fluidised bed, also with variable location. The fluidised bed is followed by a powder-metering device (D), which is separated off by a valve flap (F) and which is fed by a product overflow (8). Some of the product formed can be recycled into the spray-drying unit (B) via fly conveying, in which a fan (E) serves as conveying element, if desired after comminution (9A, 10A) or without comminution (9B, 10B). The fan (E) acting as conveying element can simultaneously serve as comminution unit for the recycled powder.

In the process for the preparation of spray-dried pulverulent β-(D)-mannitol, a) in a first step, a liquid medium, spray gas, pulverulent material and hot air are combined, b) the existing pulverulent product is precipitated into a fluidised bed, taken up, fluidised and transported further, and, if desired, c) in one or more granulation step(s), sprayed with further liquid medium, dried d) and conveyed in the fluidised bed in the direction of the powder-metering device, from which e) some of the unground and/or ground, pulverulent material is recycled into the process.

The liquid medium is preferably a solution. However, it may also be an aqueous suspension of already formed β-(D)-mannitol.

In a particular variant of the process, the recycled pulverulent material can be comminuted before the recycling.

The spray, carrier and heating gas used can be air or an inert gas selected from the group consisting of $N_2$ and $CO_2$. The gas can, in accordance with the invention, be circulated, it being freed from particles by filters or especially with the aid of dynamic filters, dried in the condenser and fed back to the spray nozzles or heated and introduced into the fluidised bed.

In order to carry out the process, the plant is initially charged with pulverulent starter material via the fill ports (3). A stream of air is produced in the spray-drying space via the chambers (1). The introduced starter material is fluidised by this stream of air and moves in the direction of the discharge flaps (F). The powder stream attains this direction of movement on generation of the air stream through a corresponding perforation of the Conidur plate. The fluidised product can be discharged by simply opening the valve flaps (F). At this point of the plant, devices are provided which enable the product to be recycled either into a powder-metering device or, via fly conveying, to the spray-drying unit. An overflow (8) for the finished product is located at the discharge above the powder-metering device. The fan (E) of the spray-drying unit serves both as conveying means for the product and as comminution unit for powder material to be recycled. Recycled powder material from the return line (9A, 9B) is combined with the corresponding media liquid (5), spray air (6) and hot air (4) through the particular design of the spray-drying nozzle. The corresponding powder or granular material is taken up by the fluidised bed and, as already described above, transported further. On passing through the granulation nozzles (C), further medium, which can have a different composition to that introduced into the spray nozzle with powder recycling, can be sprayed onto the particles formed. In this way, further granulation and re-setting of the particle size distribution can take place. The product from the chambers (1) is dried to the desired final moisture content by means of air introduced via the Conidur plates. Dynamic filters (G) integrated into the plant prevent discharge of powder particles into the environment.

Instead of the granulation nozzles (C), as shown in FIG. 1, one or more spray nozzles or spray-drying nozzles or alternatively only one, two or more than three granulation nozzles can be installed at the corresponding point of the plant. These additional nozzles may be located directly at the beginning of the fluidised bed or moved further to the back. The choice of site at which the powder material originally formed is re-sprayed one or more times is, inter alia, also dependent on the residual moisture content that the desired product is to have. It goes without saying that a product having a particularly low residual moisture content after the final spraying makes a longer residence time in the fluidised bed necessary than one having a higher residual moisture content.

As desired, different compositions can be applied through the various nozzles to the particle surfaces already formed, enabling particles having a layered structure to be obtained. However, it can also serve to achieve a more uniform particle size distribution.

It is furthermore possible to operate the plant not only with air as carrier medium. It is also possible to operate the entire plant in circulation with an inert gas, such as, for example, nitrogen or carbon dioxide.

The plant is designed in such a way that the parameters amount of liquid, spray pressure, amount of powder recycled, amount of hot gas, hot-gas temperature, amount of warm air, warm-air temperature, etc., can be regulated individually. The amount of powder recycled, the amount of liquid fed in and the spray pressure can therefore be set specifically depending on the desired properties with respect to moisture content, particle size and particle size distribution of the end product. As desired, pulverulent products having particle sizes of between 50 and 1000 $\mu$m can be produced in the plant described. Depending on the mode of operation and the process parameters selected, the particles can have a layered (onion) structure or an agglomerate structure as the case may be.

The formation of the particles can be controlled particularly by a spray nozzle integrated into the plant, which is suitable for the production of spray-dried granules. This spray nozzle is a spray system (B) which consists of a two-component spray nozzle [(1), (2), (3)], which can be heated by means of hot water and which is in turn fitted with a powder recycling system (4) arranged around the two-component spray nozzle and a surrounding hot-gas flow (5). Specifically, the powder recycling system (4) can be arranged coaxially around the two-component spray nozzle.

The advantage of this spray system is that recycled powder comes into contact immediately at the exit of the two-component spray nozzle with the liquid droplets generated via the atomisation air. In order that the powder particles do not stick together and that the surface moisture can be drawn off, the spray and powder part is included in a hot-gas stream. Subsequent drying to the desired residual moisture content takes place in the fluidised bed.

In particular also through the incorporation of this spray-drying system, it is possible to produce particle sizes specifically.

A particular advantage of this spray-drying process therefore consists in that pulverulent β-(D)-mannitol having very different properties with respect to moisture content, particle size and particle size distribution can be prepared in a single plant without further process steps for aftertreatment of the product depending on the process parameters set and on the liquid media to be atomised.

In order to obtain particularly good DC properties (DC=direct compression) of the spray-dried substance, here mannitol, it is advantageous to agglomerate the individual particles formed in the spray drying. For this purpose, a spray tower is located vertically above the fluidised bed above the spray-drying unit (B) according to the invention.

The hot aqueous mannitol solution is atomised via one or more two-component nozzle(s) (5) (6), which is (are) heated with hot water (7). The spray jet produced is surrounded by a mannitol powder recycling system (9) arranged around this nozzle and a stream of hot gas (4). The solid crystallises in the spray jet, forms agglomerates and is taken up by the fluidised bed. Hot air from the air introduction chambers (1) flows through the fluidised bed and fluidises the latter. The base of the fluidised bed is a Conidur plate, which ensures specific transport of the solid in the direction of the discharge and also produces a defined residence time of the solid in the fluidised bed. The residence time of the product in the processor can be controlled via the bed depth, spray amount and recycle quantity. The solid is transported through a plurality of air introduction chambers (1) connected in series and dried to a residual moisture content of <0.3%. The drying operation takes place over the length of the fluidised bed in a certain temperature profile in order to prevent overheating of the product.

The water-laden and dust-containing fluidisation air is cleaned via dynamic filters (G) and discharged via the waste-air chambers (2). The dynamic filters are regularly cleaned by means of pulses of compressed air. The dust cleaned off binds the spray mist from the spray zone and prevents settling and baking of solid onto the walls.

The dried solid falls into a metering system for recycling (D) via double pendulum flaps (F) or other discharge systems. The discharged product can optionally be worked-up further via a classification system. The oversize particles (and undersize particles) formed can be ground in the fan (E) above the powder recycling system (9) and recycled into the spray drier together with the undersize particles, i.e. with dust-form mannitol powder having particle sizes of less than 75 $\mu$m, in particular less than 40 $\mu$m.

A sub-stream is discharged as finished product (8) at the outlet. The product can be classified via a sieve, it being possible for the oversize particles or residual material, i.e. the coarse powder fraction, to be recycled via the suction side of the grinding fan (9A), ground and returned to the process. Inter alia, this minimises product losses.

The fan (E) of the spray-drying unit serves both as conveying means for product to be recycled (introduction of solid on the pressure side (9B)) and as comminution unit for recycled powder material (introduction of solid on the suction side (9A)). The two sub-streams of solid are controlled, for example, via the rotational speed of the star valves (10A, 10B). Recycled powder material from the return lines (9) is, as already described above, combined with the corresponding media liquid (mannitol solution) (5), spray air (6) and hot air (4) through the particular design of the spray-drying nozzle.

The feed air is fed to the fan (E) from the product discharge zone of the processor. In this way, the fine dust (<15 $\mu$m) is removed from the product at the same time (pneumatic classification). At the same time, the removal of this fine dust has the effect that greater tablet hardness values can be achieved on use of this product freed from fine dust.

In the case of sub-stream 9B, the option exists of screening the oversize particles (residual material) out of the recycling system after the star valve 10B in order to be able to control the process better. These oversize particles (residual material) can be introduced on the suction side into the grinding fan (E) or another comminution machine, ground and fed back to the process.

As already indicated above, the quality of the agglomerates and thus of the product can be controlled via the plant parameters, such as concentration, spray pressure, temperature, spray amount, amount of recycled powder, amount of principal air, dust extraction, bed depth, etc. A reduction in the height of the spray nozzle [(B)→(C)] above the fluidised bed enables the particle structure to be converted from an agglomerate (berry structure) into granules (onion structure). At the lowest possible arrangement of the nozzles (granulation nozzles (C)), the powder recycling (9) can take place via the fill ports (3). In order to obtain a product for direct compression continuously, both the particle structures and the modification, particle size distribution, water content, density, etc., must be monitored. It has been found that the best product for compression is obtained if mannitol is crystallised out in a fine needle structure.

Contamination by other mannitol modifications in the mannitol powder impairs the compression properties. In particular, it has been found that, especially, increasing contents of α-mannitol have an adverse effect on the compressibility, the achievable tablet hardness values and the surface quality of the tablets. In products produced by the process according to the invention, no α-mannitol per se can be detected, in particular in mannitol which has a content of the β-modification of greater than 95% by weight, in particular greater than 98% by weight.

FIG. 1 shows a 500× enlargement of an SEM photograph of a product having a content of the β-modification of greater than 98%.

Experiments have shown that it is necessary to maintain and monitor the set parameters of the spray-drying process in order to obtain pure β-mannitol which has constant, good compression properties.

In accordance with the invention, use is preferably made as starting material of D-mannitol having a purity of >90%, particularly preferably having a purity of >95% and very particularly preferably having a purity of >98%. This starting material is employed in the form of an aqueous 40–50% solution and is atomised into the plant at a temperature in the range from 60 to 95° C. The solution is preferably heated to a temperature in the range from 70 to 85° C., in particular from 75 to 80° C., before the atomisation.

In accordance with the invention, solutions having different mannitol concentrations can be employed at different points of the plant. Thus, it has proven appropriate to charge spray nozzles above the fluidised bed in the direction of the product discharge with solutions having higher mannitol concentrations than spray nozzles located at the beginning of the fluidised bed. It is therefore possible to employ a solution having a mannitol concentration of about 60% by weight, based on the solution as a whole, at the end of the fluidised bed, whereas the two-component nozzle with powder recycling is preferably operated with an approximately 40–50% aqueous solution. In this way, the product properties can again be influenced in the desired sense, it being necessary to observe the plant parameters precisely in this procedure.

Through variation of the parameters spray pressure, amount of liquid, amount of powder recycled, hot-air stream and hot-air temperature, particle sizes of between 50 and 1000 μm can be set specifically.

It has furthermore been found that the parameters of the plant used in accordance with the invention have to be set as follows in order to obtain a uniform product:

The spray pressure of the two-component nozzles should be set in the range 2–4 bar, preferably in the range from 2.5 to 3.5 bar. The amount of hot gas fed to the two-component nozzle should be regulated in such a way that from about 1.5 to 3 m$^3$/(h kg of solution) at a temperature of from about 80 to 110° C. are conveyed. It has been found that, with a relatively high feed of hot gas, better product quality is obtained if a relatively low temperature is used. The powder recycling should be set in accordance with the invention in such a way that solids recycling takes place in the range 0.2–2.0 kg of solid/(h kg of solution), preferably in the range from 0.5 to 1.5 kg of solid/(h kg of solution). The process is particularly favourable if the solids recycling is in the range from 0.5 to 1.0 kg of solid/(h kg of solution).

In order to carry out the process, pre-heated air must be fed into the plant. Good results are achieved if the air fed to the plant is pre-heated to a temperature in the range 45–120° C. It is favourable for the process according to the invention if the feed air has a temperature in the range from 65 to 110° C. It is particularly advantageous for the formation of a β-mannitol powder having good compression properties if the temperature of the feed air fed in is in the range from 70 to 100° C. The amount of feed air supplied should be regulated in accordance with the invention in such a way that 1000–2000 m$^3$/m$^2$ per hour, in particular from 1200 to 1700 m$^3$/m$^2$ per hour, are fed into the plant.

In combination with the other parameters set, favourable process conditions exist if the air stream in the plant is set in such a way that the waste-air temperature is in the range 30–50° C.

It has furthermore proven favourable to regulate the process conditions in such a way that the amount of powder located in the fluidised bed is set to an amount of 50–150 kg/m$^2$ of bed. It is particularly favourable if the amount of powder is in the range 80–120 kg/m$^2$ of bed.

It has also been found that the process can be controlled, in particular, by specific recycling of a powder having a selected particle size.

As can be seen from the plant diagram, powder recycling can be carried out both by powder withdrawal from the fluidised bed and by recycling of a very finely divided powder fraction which is formed during finishing, i.e. during homogenisation of the particle size by screening and packaging of the resultant product.

It is also possible, prior to recycling, to comminute powders having relatively large particle cross sections in the fan (E) of the spray-drying unit. As already indicated above, the powder stream can be controlled by adjusting the rotational speed of the star valves (10A, 10B). In order to grind powder to be recycled to the desired particle size before the recycling, the rotational speed of the star valve 10A (B) should accordingly be set in such a way that recycling takes place via the fan with grinding.

Experiments have shown that the equilibrium can be shifted towards the formation of β-mannitol if the mean particle size of the recycled powder ground in the fan (E) is less than 75 μm. β-mannitol is particularly preferably formed if the mean particle size of the recycled powder is less than 40 μm. Surprisingly, it has been found that recycling of a powder having particle sizes of less than 20 μm gives mannitol powders having a proportion of the β-fraction of greater than 90%. It has particularly surprisingly been found that, in particular, recycling of the so-called dust fraction which is formed in the product discharge zone of the processor and is usually removed from the product, results in a uniform product having a particularly high proportion of the β-fraction. The mean particle size of the dust fraction is in the range from about 1 to 20 μm, in particular in the range from 3 to 15 μm. In addition, it has been found that the dust from the recycling results in stable operation in the spray zone of the processor.

Since grinding in the fan (E) only gives these particle sizes with particular effort, the "dust-form" product fraction from the powder-metering device, which is formed in the plant in line (9A), is preferably recycled into the spray drying, in particular at the beginning of the process, by controlling the rotational speed of the star valve 10A by grinding. By simultaneously reducing the rotational speed of the star valve 10B, recycling of coarse mannitol fraction is reduced.

Surprisingly, it has been found that, after the equilibrium has been established in the direction of the formation of β-mannitol in a purity of greater than 95%, the process can be continued in a stable manner if the powder ground in the fan to a particle size of less than 75 μm is likewise recycled.

In this way, it is possible, surprisingly, to set the spray-drying process by exclusive recycling of the "dust fraction" formed by suitable regulation of the rotational speeds of the star valves 10A and 10B at the beginning in such a way that only β-mannitol is formed. The relatively coarse fraction (the so-called oversize particles) of the mannitol powder formed can subsequently again also be recycled into the process without risking shifting the equilibrium. This has the advantage that adhesion of the particularly finely divided spray mist to the walls of the plant in long-term operation can be avoided and interruptions to the process can be prevented.

A suitable choice of the process parameters enables production of a product having a content of the β-modification of greater than 90%. Constant monitoring of the product quality produced enables the fraction to be increased readily to a content of the β-modification to greater than 95%.

In particular if the above-described plant parameters are set to the optimum and the other process parameters are monitored, the product obtained in the process according to the invention is a mannitol having the following properties:
   mannitol for direct compression
   purity of the β-modification >98%
   bulk density 350–500 g/l
   residual moisture content <0.3%
   particle distribution: $x_{50}$ at 200 μm: <10%<53 μm+<15%>500 μm $x_{50}$ at 300 μm: <10%<100 μm+<10%>850 μm $x_{50}$ at 450 μm: <5%<100 μm+<10%>850 μm Since the various modifications of the mannitol are very similar, they cannot be differentiated in the DSC on the basis of their melting points usually measured in analysis. Identification is only possible, for example, by means of X-ray or NIRS.

However, owing to the tablet hardness values achieved with the resultant product, significant differences from commercially available products are evident. Compared with a commercially available product which has a relatively high content of the β-modification in the pulverulent mannitol, tablets having hardness values which are from about 45 to 70% higher are obtained with the β-mannitol prepared in accordance with the invention.

For better understanding and in order to illustrate the invention, a general flow chart (FIG. 1) of the spray-drying plant described is given below, along with examples which are within the scope of protection of the present invention, but are not suitable for restricting the invention to these examples.

Figure 2:
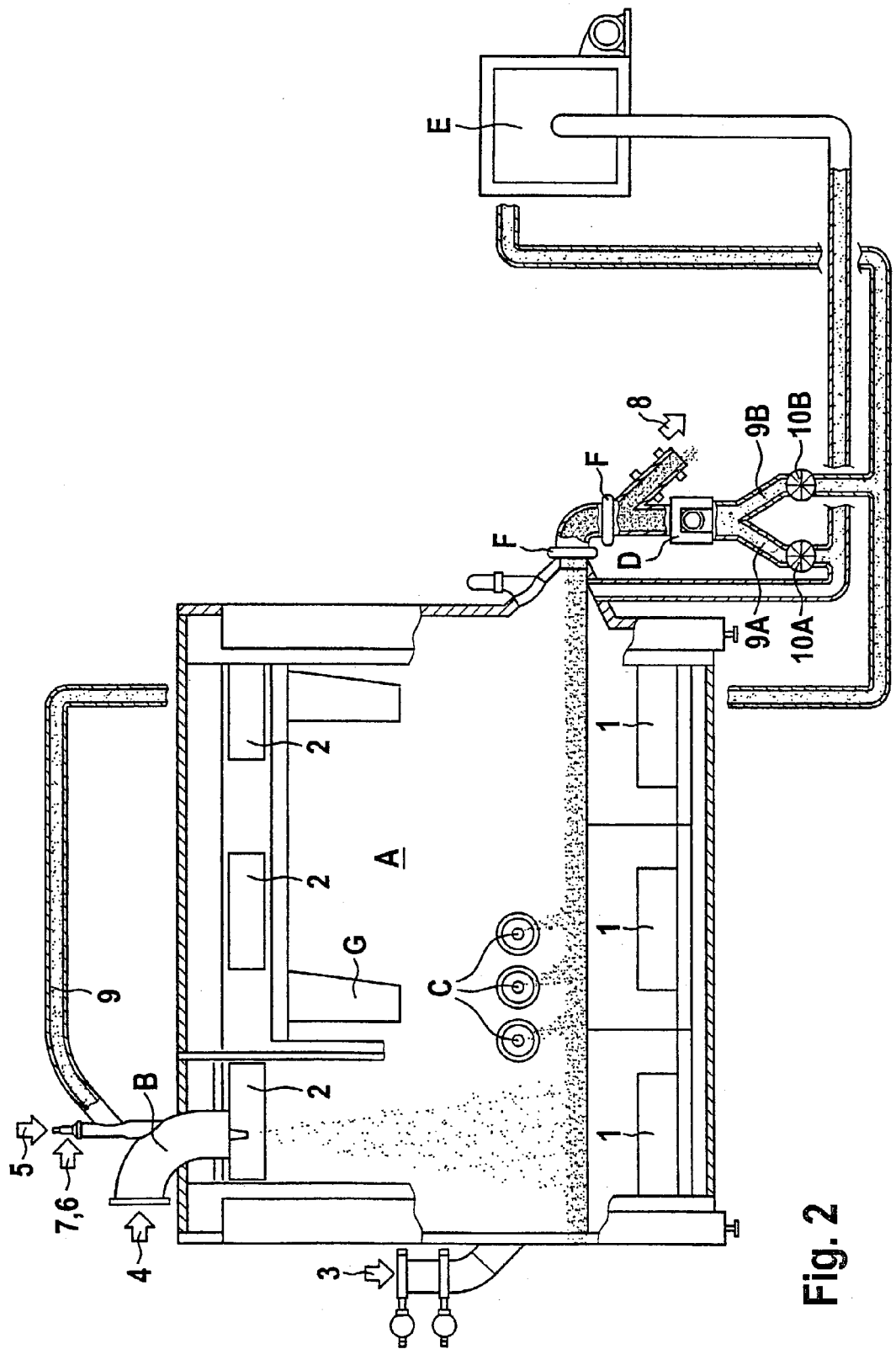

FIG. 2 shows a generalised flow chart of a possible embodiment of a spray-drying plant employed for carrying out the process, in which the numbers and letters given have the following meanings:
   1 Air introduction chambers
   2 Heating devices
   3 Fill ports
   4 Hot-air feed
   5 Liquid feed
   6 Spray air
   7 Heating medium
   8 Product
   9 Powder
   (9A finely divided powder (dust), 9B coarse powder)
   10 Star valve (10A and 10B) for regulating the powder recycling
   A Fluidised-bed apparatus
   B Spray-drying unit
   C Granulation nozzles
   D Powder-metering device
   E Fan for powder recycling
   F Valve flaps
   G Dynamic filter With reference to the components mentioned in the description and given in the flow chart, it is readily possible for the person skilled in the art to produce an appropriate plant for carrying out the process by selecting commercially available individual components. It goes without saying for the person skilled in the relevant art that both additional electrical and mechanical control units have to be installed for operation of the plant in order to be able to regulate and vary the parameters in the process according to the invention, as described.

The following examples for the preparation of various DC β-mannitol grades serve to explain the present invention in greater detail.

EXAMPLE 1

Preparation of a DC β-mannitol Having a Mean Particle Size $X_{50}$=200 μm

For preparation, the spray-drying plant is filled with about 70 kg/m² of β-mannitol as the bed. (This initially introduced bed should as far as possible have the desired product properties. If the bed material available should have other properties, the plant must be started up under gentle conditions until the equilibrium has shifted in the desired direction.)

As fluidisation and feed air, the plant is operated with 1200 m³/m² h at a temperature of about 70° C. (Before start-up of the plant, it must be ensured that sufficient dust is present in the plant. Dust can be generated via the powder-metering device (D), the suction-side recycling system (9A) and metering device (10A) via the/with the fan (E) and blown into the plant). When sufficient dust is in the plant, the metering (10A) of the recycle is reduced, and the atomisation of mannitol solution is begun. The atomised solution has a concentration of about 40% and a temperature of about 75° C. At a spray pressure of about 3 bar (spray medium is air), about 45 $kg/m^2$ h of solution are atomised in the plant. About 0.5 kg of solid/(h kg of solution) is recycled into the spray zone via the recycling system (9, 10) via the powder-metering device (D). The star wheels (10A, 10B) are set in such a way that a sufficient amount of product (9A, 10A) is always ground in the fan (E) and conveyed back into the plant with the unground product (9B, 10B).

Evaporation of the water in the plant causes the formation of an equilibrium with a bed temperature of about 35–40° C. The waste-air temperature is about 30–33° C. (It must be ensured that the waste air is saturated as far as possible (about 80–90% rel. humidity). This is advantageous for the efficiency of the process and for the mannitol crystallisation process.) In this way, the best crystal structure and the purest β-modification of the mannitol are obtained. Since the fan (E) takes its feed air from the product discharge zone before the valve flaps (F) of the plant (A), and the discharged product is thus dust-free due to the pneumatic classification, β-mannitol with excellent properties for direct compression is obtained at the product outlet (8). In order to obtain DC β-mannitol having the desired particle size distribution, it can be sieved after the discharge valve (F), i.e. before the product outlet (8) and the powder-metering device (D). It is advantageous for the process also to sieve the oversize particles out of the product to be recycled (9B, 10B), since they otherwise accumulate further in the spray zone and can cause problems in the fluidised bed. The undersize and oversize particles sieved out can be fed on the suction side to the fan (E), ground and fed back into the process together with the other recycled solids sub-streams (9A, 10A, 9B, 10B). In this way, product losses are minimised, and the process runs in a more stable manner through the additional dust recycling (ground product).

EXAMPLE 2

Preparation of a DC β-mannitol Having a Mean Particle Size $X_{50}$=300 μm

As described in Example 1, the spray-drying plant is, for preparation, filled with about 100 $kg/m^2$ of β-mannitol as the bed and started up.

As fluidisation and feed air, the plant is operated with 1500 $m^3/m^2$ h at a temperature of about 85° C. The mannitol solution to be atomised has a concentration of about 45% by weight at a temperature of about 80° C. At a spray pressure of about 3 bar (spray medium is air), about 65 $kg/m^2$ h of solution is atomised in the plant. The star wheels (10A, 10B) are set in such a way that a sufficient amount of product (9A, 10A) is always ground in the fan (E) and conveyed back into the plant with the unground product (9B, 10B). Evaporation of the water in the plant causes the formation of an equilibrium with a bed temperature of about 40° C. The waste-air temperature is about 35–40° C. It must be ensured that the waste air is saturated as far as possible (about 80–90% rel. humidity). The oversize particles from the product to be recycled (9B, 10B) are sieved out, since they otherwise accumulate further in the spray zone and cause problems in the fluidised bed. The undersize and oversize particles sieved out are fed on the suction side to the fan (E) and ground. They are fed back into the process together with the other recycled solids sub-streams (9A, 10A, 9B, 10B).

EXAMPLE 3

Preparation of a DC β-mannitol Having a Mean Particle Size $X_{50}$=450 μm

As described in Example 1, the spray-drying plant is, for preparation, filled with about 120 $kg/m^2$ of β-mannitol as the bed. As fluidisation and feed air, the plant is operated with 1700 $m^3/m^2$ h at a temperature of about 100° C.

The hot gas is fed to the spray zone in an amount in the order of about 1.6 $m^3$/(h kg of solution) at a temperature of about 80° C. When all these parameters have been set, atomisation of mannitol solution can be begun.

The solution has a mannitol concentration of about 50% by weight at a temperature of about 90° C. At a spray pressure of about 3.5 bar (spray medium is air), about 100 $kg/m^2$ h of solution are atomised in the plant. About 0.8–1.0 kg of solid/(h kg of solution) are recycled into the spray zone via the powder-metering device (D) via the recycling system (9, 10). The star wheels (10A, 10B) are set in such a way that a sufficient amount of product (9A, 10A) is always ground in the fan (E) and conveyed back into the plant with the unground product (9B, 10B).

Evaporation of the water in the plant causes the formation of an equilibrium with a bed temperature of about 40–45° C. The waste-air temperature is about 40° C. It must be ensured that the waste air is saturated as far as possible (about 80–90% rel. humidity).

The oversize particles from the product to be recycled (9B, 10B) are sieved out since they otherwise accumulate in the spray zone and cause problems in the fluidised bed. The undersize and oversize particles sieved out are fed on the suction side to the fan (E) and ground. They are fed back into the process together with the other recycled solids sub-streams (9A, 10A/9B, 10B).

What is claimed is:

1. A process for the preparation of mannitol for direct compression having a content of the β-modification of greater than 90%, comprising:

a) combining an aqueous D-mannitol solution as a starting material, spray gas, pulverulent β-mannitol and hot gas, and b) precipitating a resultant pulverulent product into a fluidized bed wherein the resultant pulverulent product is taken up, fluidized and further transported in the bed.

2. A process according to claim 1, further comprising recycling some of the pulverulent product into the process.

3. A process according to claim 1, further comprising spraying the resultant powder in one or more granulation step(s), with a further liquid medium, drying and further transporting in the fluidized bed.

4. A process according to claim 1, wherein the mannitol solution is made of D-mannitol having a purity of ≧90%.

5. A process according to claim 1, wherein the mannitol solution is made of D-mannitol having a purity of >98%.

6. A process according to claim 1, further comprising recycling the β-mannitol formed as a dust fraction from a product discharge zone of a processor into a spray-drying unit for shifting the equilibrium towards the formation of β-mannitol.

7. A process according to claim 6, wherein the β-mannitol has a mean particle size of less than 20 μm.

8. A process according to claim 6, wherein the β-mannitol dust fraction formed in a line is recycled into the spray-drying unit from a powder-metering device as the pulverulent β-mannitol by controlling a rotational speed of a star valve via a fan.

9. A process according to claim 1, further comprising after establishing the equilibrium, recycling pulverulent β-mannitol having a mean particle size of less than 75 μm.

10. A process according to claim 1, further comprising after establishing the equilibrium, recycling the unground β-mannitol.

11. A process according to claim 9, further comprising comminuting the recycled pulverulent material before the recycling, by grinding in a fan, which simultaneously serves as a conveying element for the powder recycling.

12. A process according to claim 1, further comprising regulating the rotational speeds of star valves and grinding of a coarse product formed to a particle size of less than 75 μm in a fan before recycling into a spray-drying unit to result in an exclusive formation of β-mannitol.

13. A process according to claim 1, further comprising employing an aqueous 40–50% D-mannitol solution as a starting material and atomizing at a temperature of 60–95° C.

14. A process according to claim 1, wherein air, $N_2$ or $CO_2$ is both the spray gas and a carrier and heating gas.

15. A process according to claim 1, further comprising circulating the gas, and freeing a circulated gas from particles by filters, drying in the condenser and feeding back to the spray nozzles or heating and introducing into the fluidized bed.

16. A process according to claim 15, wherein the gas is freed from particles with the aid of dynamic filters.

17. A process according to claim 3, wherein the liquid media comprise different compositions.

18. A process according to claim 1, further comprising producing particle sizes of 50–1000 μm by varying a spray pressure, a spray amount, a mannitol concentration, an amount of powder recycled, a hot-air stream and a hot-air temperature.

19. A process according to claim 18, further comprising pre-heating the air fed to a plant to a temperature of 45–120° C., supplying 1000–2000 $m^3/m^2$ feed air per hour, and giving a waste-air temperature of 30–50° C.

20. A process according to claim 18, further comprising setting the spray pressure of the two-component nozzles of 2–4 bar, and feeding about 1.5 to 3 $m^3/h$ kg of solution of hot gas having a temperature of about 80–110° C. to the two-component nozzle.

21. A process according to claim 18, further comprising recycling 0.2–2.0 kg of solid/h kg of solution powder.

22. A process according to claim 18, further comprising setting the amount of powder present in the fluidized bed to an amount of 50–150 $kg/m^2$ of bed by adjusting a spray pressure, an amount of liquid, a mannitol concentration, an amount of powder recycled, a hot-air stream and a hot-air temperature.

23. A process for preparing mannitol for direct compression having a content of the β-modification of greater than 90%, comprising combining an aqueous D-mannitol solution and pulverulent β-mannitol for precipitating a resultant pulverulent product into a fluidized bed.

* * * * *